(12) United States Patent
Rock et al.

(10) Patent No.: US 6,524,245 B1
(45) Date of Patent: Feb. 25, 2003

(54) MEDICAL DIAGNOSTIC ULTRASOUND IMAGING SYSTEM AND METHOD FOR NETWORK MANAGEMENT

(75) Inventors: David A. Rock, Saline, MI (US); David E. Fenstemaker, Mountain View, CA (US); Jeffrey S. Hastings, Los Altos, CA (US)

(73) Assignee: Acuson, Corp., Mountain View, CA (US)

( * ) Notice: Subject to any disclaimer, the term of this patent is extended or adjusted under 35 U.S.C. 154(b) by 0 days.

(21) Appl. No.: 09/632,546

(22) Filed: Aug. 4, 2000

(51) Int. Cl.$^7$ ................................................ A61B 8/00
(52) U.S. Cl. ................................. 600/437; 128/905
(58) Field of Search .................. 600/437; 422/67; 707/205, 204; 345/792; 128/905

(56) References Cited

U.S. PATENT DOCUMENTS

| | | | |
|---|---|---|---|
| 5,603,323 A | | 2/1997 | Pflugrath et al. |
| 5,715,823 A | | 2/1998 | Wood et al. |
| 5,851,186 A | * | 12/1998 | Wood et al. ............... 600/437 |
| 5,897,498 A | * | 4/1999 | Canfield et al. ............ 600/437 |
| 5,938,607 A | * | 8/1999 | Jago et al. .................. 600/437 |
| 6,224,551 B1 | * | 5/2001 | Mullen ........................ 600/437 |
| 6,256,643 B1 | * | 7/2001 | Cork et al. .................. 422/67 |

* cited by examiner

Primary Examiner—Marvin M. Lateef
Assistant Examiner—Ruby Jain

(57) ABSTRACT

The preferred embodiments described herein provide a medical diagnostic ultrasound imaging system and method for network management. In one preferred embodiment, a medical diagnostic ultrasound imaging system network is presented comprising first and second medical diagnostic ultrasound imaging systems coupled with a processor. An error message is sent from the first medical diagnostic ultrasound imaging system to the processor, and the processor automatically analyzes and responds to the error message. In another preferred embodiment, configuration information from the first and second medical diagnostic ultrasound imaging systems is sent to the processor. Based on the configuration information sent from the first medical diagnostic ultrasound imaging system, the processor automatically selects a software application from a plurality of software applications and sends the selected software application to the first medical diagnostic ultrasound imaging system.

16 Claims, 3 Drawing Sheets

MEDICAL DIAGNOSTIC ULTRASOUND IMAGING SYSTEM AND METHOD FOR NETWORK MANAGEMENT

BACKGROUND

Medical diagnostic ultrasound imaging systems can be coupled in a network arrangement to allow images generated by the systems to be available to users of the network. Because current network management procedures often require the use of one or more service technicians, the costs associated with these current procedures can be disproportionately high with respect to the cost of the ultrasound system, especially for low-cost ultrasound systems. For example, if there is a problem with one of the imaging systems on the network, a user of the network phones a technician at a remote service center to verbally report the problem. A remotely-located technician can also contact the ultrasound system via a modem or network connection to remotely query the ultrasound system for diagnostic or configuration information, as described in U.S. Pat. Nos. 5,603,323 and 5,715,823. Based on the type of problem being reported and any previously-reported problems, the technician decides whether to schedule an appointment to inspect the troubled ultrasound device or merely make a record of the problem. In addition to the relatively high cost associated with this procedure, it is often difficult for the technician at the remote service center to assess the severity of the problem since the record of reported problems is often incomplete. Installing new software applications can also be a relatively costly procedure since it often requires a service technician to decide what version of the software application to install.

There is, therefore, a need for an improved medical diagnostic ultrasound imaging system and method for network management that will overcome these disadvantages.

SUMMARY

The present invention is defined by the following claims, and nothing in this section should be taken as a limitation on those claims.

By way of introduction, the preferred embodiments described below provide a medical diagnostic ultrasound imaging system and method for network management. In one preferred embodiment, a medical diagnostic ultrasound imaging system network is presented comprising first and second medical diagnostic ultrasound imaging systems coupled with a processor. An error message is sent from the first medical diagnostic ultrasound imaging system to the processor, and the processor automatically analyzes and responds to the error message. In another preferred embodiment, configuration information from the first and second medical diagnostic ultrasound imaging systems is sent to the processor. Based on the configuration information sent from the first medical diagnostic ultrasound imaging system, the processor automatically selects a software application from a plurality of software applications and sends the selected software application to the first medical diagnostic ultrasound imaging system.

The preferred embodiments will now be described with reference to the attached drawings.

DETAILED DESCRIPTION OF THE PRESENTLY PREFERRED EMBODIMENTS

Network Overview

Figure 1:
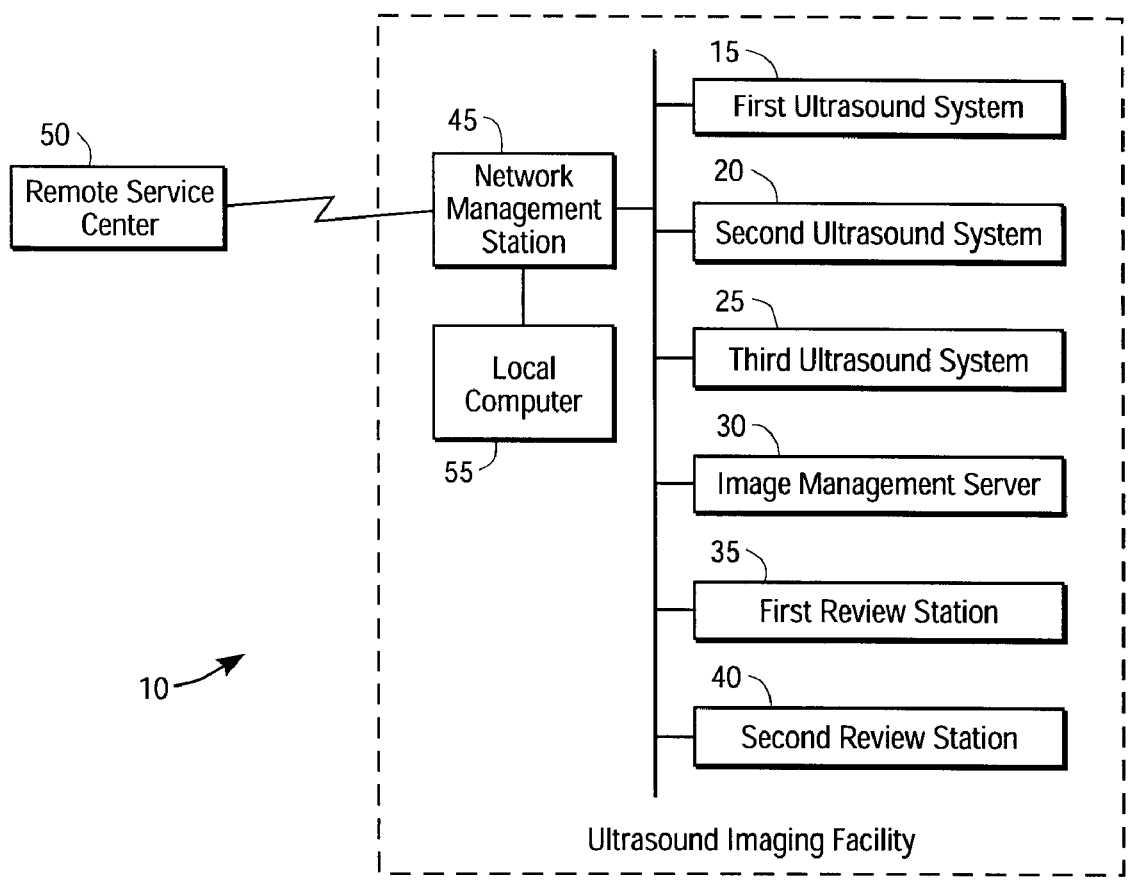
FIG. 1 is a block diagram of a medical diagnostic ultrasound imaging network of a preferred embodiment.

FIG. 1 is a block diagram of a medical diagnostic ultrasound imaging network 10 of a preferred embodiment. In this preferred embodiment, the network 10 is a local network in an ultrasound imaging facility (e.g., a hospital, clinic, or laboratory). As shown in FIG. 1, the network 10 comprises a plurality of medical diagnostic ultrasound imaging systems 15, 20, 25, an image management server 30, and a plurality of image review stations 35, 40. The network also comprises a network management station 45 that is coupled with each of the components in the network 10 and is further coupled with a remote service center 50 and a local computer 55. As used herein, the term "coupled with" means directly coupled with or indirectly coupled with through one or more components through physical and/or wireless connections. Each of these components will be discussed below.

Figure 2:
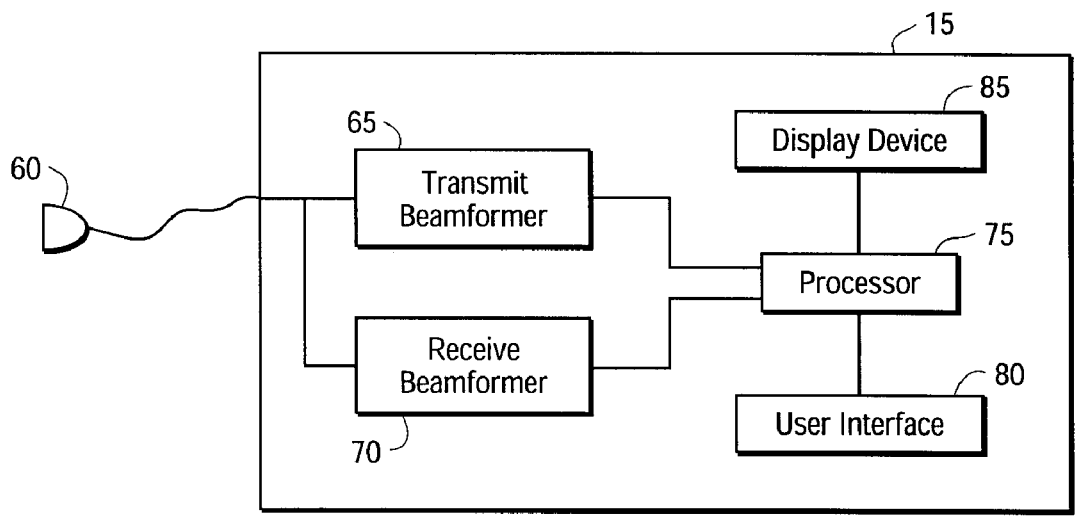
FIG. 2 is a block diagram of a medical diagnostic ultrasound imaging system of a preferred embodiment.

FIG. 2 is a block diagram of one of the ultrasound imaging systems 15 in the network. This ultrasound system 15 comprises a transducer 60 coupled with a transmit beamformer 65 and a receive beamformer 70. The beamformers 65, 70 are each coupled with a processor 75, which is coupled with a user interface 80 and a display device 85. The ultrasound system 15 can be used with any suitable imaging mode (e.g., B-mode imaging, Doppler imaging, tissue harmonic imaging, contrast agent harmonic imaging, etc.) and with any suitable transducer 60 (e.g., 1 D, 1.5 D, plano-concave, single element, phased-array, etc.). In operation, the processor 75 causes the transmit beamformer 65 to apply a voltage to the transducer 60 to cause it to vibrate and emit an ultrasonic beam into an object, such as human tissue (i.e., a patient's body). Ultrasonic energy reflected from the body impinges on the transducer 60, and the resulting voltages created by the transducer 60 are received by the receive beamformer 70. The processor 75 processes the sensed voltages to create an ultrasound image associated with the reflected signals and displays the image on the display device 85. The user interface 80 can be used to control functions of the ultrasound imaging system 15, such as adjusting parameters used in the transmit, receive, display, and image storage operations.

Still and/or dynamic diagnostic medical ultrasound images and any non-image data, such as calculation and patient data, generated by the ultrasound systems during a diagnostic examination can be stored in a storage device (e.g., a hard drive or local disk) in the image management server 30. Image and non-image data can be retrieved from the image management server 30 and viewed by one of the review stations. As used herein, a "review station" refers to any device that can view ultrasound images. A review station typically comprises a processor, a display device, and a user interface and can take the form of a personal computer or workstation. A review station can run an application that analyzes, creates, and/or alters the image or non-image data. Any altered data can also be stored in the image management server 30.

The network management station 45 comprises a processor that is used in these preferred embodiments to analyze error messages from the ultrasound systems in the network 10 and/or to provide the ultrasound systems in the network 10 with a software application. As used herein, the term "processor" broadly refers to the hardware and/or software components that can be used to implement the functionality described with respect to the processor. It should be understood that any appropriate hardware (analog or digital) or software can be used and that the embodiments described herein can be implemented exclusively with hardware. Further, a "processor" can be separate from or combined with (in whole or in part) other processors (including attendant processors). In one presently preferred embodiment, the network management station 45 takes the form of a low-cost personal computer in an enclosure box comprising a Pentium-class processor using the Linux operating system, a hard disk, an Ethernet card, and one or more internal modems. When the network management station 45 is used in an imaging facility that is not controlled by the provider of the network management station 45, it may be preferred to equip the network management station 45 without a monitor, keyboard, or removable disk to prevent unauthorized local access to the network management station 45. While the network management station 45 can be externally located and communicate with the ultrasound systems on the network 10 via an external connection (such as an Internet connection), it is preferred that the network management station 45 be part of the local network 10 (e.g., an intranet) and communicate with the ultrasound systems in a local-network fashion. In this way, the functions of the network management station 45 will be available even when an external network connection is unavailable.

As described above, the processor of the network management station 45 can be used to analyze error messages from the ultrasound systems in the network 10 and/or to provide the ultrasound systems in the network 10 with a software application. These applications will be described in more detail below.

Error-Message-Analysis Embodiments

Figure 3:
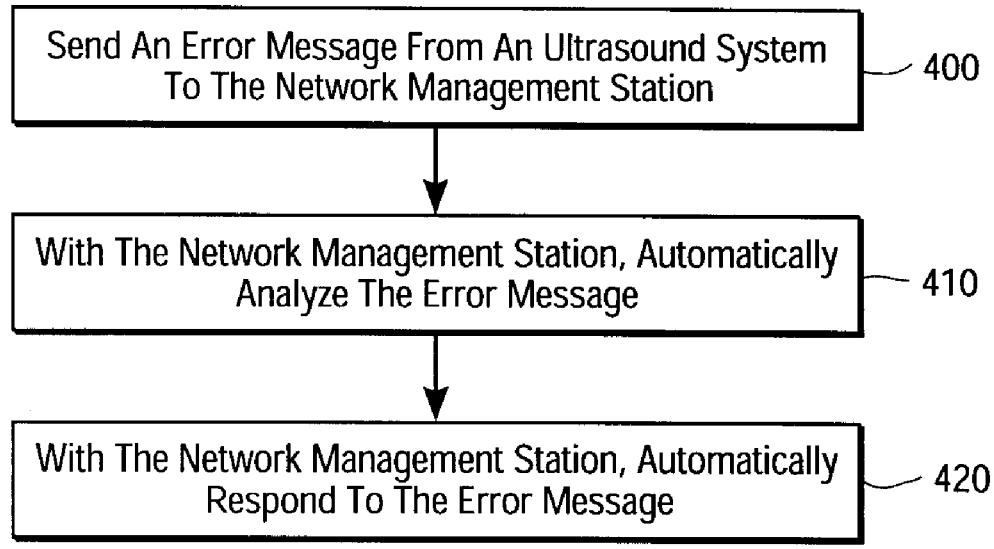
FIG. 3 is a flow chart of a method for responding to an error message from a medical diagnostic ultrasound imaging system of a preferred embodiment.

In one preferred embodiment, the processor of the network management station 45 is used to analyze error messages from the ultrasound systems in the network 10. This preferred embodiment will be illustrated in conjunction with the flow chart of FIG. 3. As shown in the flow chart of FIG. 3, an error message is sent from the first medical diagnostic ultrasound imaging system 15 to the network management station 45 (act 400). It is preferred that the error message comprise enough information to aid the network management station 45 in determining how to respond to the error message. For example, the error message can contain one or more of the following types of information: the application in the ultrasound system in which the error occurred, the location in the computer code of the application where the error occurred, an error code indicating the type of error, and the severity of the error (e.g., informational, warning, fatal). Appendix I contains an error message format and output fields of a presently preferred embodiment.

After receiving the error message, the network management station 45 automatically analyzes the error message (act 410). In one preferred embodiment, the network management station 45 queries a table or binary decision tree with at least some of the information sent in the error message to determine what action to take. For example, if a table cross-references error code "A" with "Response 1" and error code "B" with "Response 2," the network management station 45 would perform Response 1 if error code A is received from an ultrasound system. As another example, a binary decision tree may indicate that "Response 1" should be taken if the error message contains error code "A" and an indication that the error is "informational" but that "Response 2" should be taken instead if the error message contains error code "A" and a "fatal" indication. The analysis can also include consideration of which ultrasound system on the network 10 sent the error message. In this way, the network management station 45 can respond to the same error differently depending on the system that is experiencing the error. For example, the network management station 45 can determine that "Response 1" should be performed if a particular error message is sent from the first ultrasound system 15 but that "Response 2" should be performed if the same error message is sent from the second ultrasound system 20. In this way, less drastic measures can be taken for a less critical device.

Based on its analysis of the error message, the network management station 45 automatically responds to the error message (act 420). For example, if the network management station 45 determines that the error is not serious enough to warrant immediate attention, the network management station 45 can respond to the error message by logging the error in an error log, which can be locally or remotely analyzed by service personnel at a later time. As another example, the network management station 45 can send a command to the ultrasound system to remedy the error. In one embodiment, the network management station 45 responds to an error indicating that a software application cannot continue to run on the ultrasound system by sending a command to the ultrasound system to restart the application. In another example, if the network management station 45 determines that the error is serious enough to warrant attention, the network management station 45 can respond to the error message by sending a message to service personnel to alert them of the error. The message can take any suitable form including, but not limited to, a phone call, a pager message, a voice-mail message, a fax, an e-mail, and a posting to a network or dedicated bulletin board. The network management station 45 can also send a message to a processor in the remote service center 50 to alert it of the error. As used herein, the term "remote service center" broadly refers to any remote location with a processor that can communicate with the processor of the network management station 50. In one preferred embodiment, the remote service center 50 is responsible for the service of the ultrasound systems on the network 10. In response to the message from the network management station 45, the processor at the remote service center can take immediate action (such as providing the network management station 45 with instructions on how to respond to the error message) or can log the error message for later analysis. It should be understood that one or multiple responses can be taken (e.g., send a message to service personnel and send a command to the ultrasound system to remedy the error).

Figure 4:
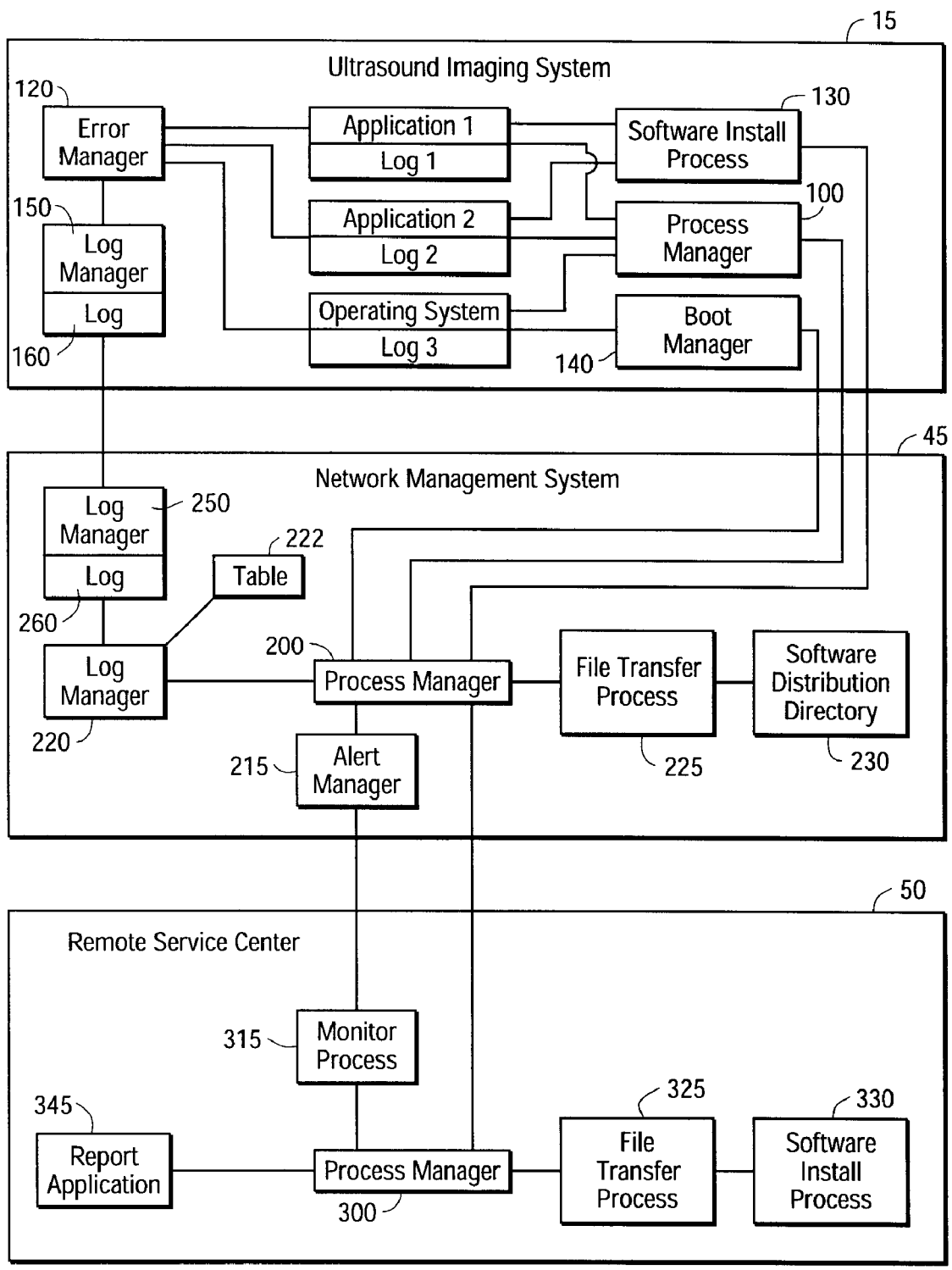
FIG. 4 is a block diagram illustrating some of the functions implemented on a medical diagnostic ultrasound imaging system, a network management station, and a remote service center of a preferred embodiment.

Turning again to the drawings, FIG. 4 is a block diagram of a presently preferred embodiment that illustrates some of the functions implemented with the processors of the ultrasound system 15, the network management station 45, and the remote service center 50. As shown in FIG. 4, the ultrasound imaging system 15 comprises a plurality of applications (Application 1, Application 2, Operating System), each associated with a respective log (Log 1, Log 2, Log 3). The ultrasound imaging system 15 also comprises a process manager 100, an error manager 120, a software install process 130, a boot manager 140, and a log manager 150 with an associated log 160. The network management station 45 comprises a process manager 200, an alert manager 215, a log monitor 220 with an associated table 222, a file transfer process 225, a software distribution directory 230, and a log manager 250 with an associated log 260. By way of overview, the log monitor 220 in the network management station 45 analyzes error messages sent from the ultrasound system 15 by consulting table 222 and communicates the response to the error to the process manager 200 of the network management station 45. The remote service center 50 comprises a process manager 300, a monitor process 315, a file transfer process 325, a software install process 330, and a report application 345.

The following example is provided to illustrate the operation of these functions. When the ultrasound imaging system 15 is turned-on, the operating system and each of the applications of the ultrasound imaging system 15 make a connection to the error manager 120. In this example, an error (such as a memory access error) prevents Application 1 from being able to operate. Application 1 creates an exception in Log 1, which is detected by the error manager 120. The error manager 120 formats and logs the exception in log 160. The log manager 150 then forwards the message through the local network 10 to the network management station 45. The log manager 250 of the network management station 45 receives the message and logs it in its associated log 260. The log monitor 220 detects a new message in the log 260 and looks up the message in the table 222, where it finds an entry that tells it to forward a message to the process manager 200 of the network management station 45 to restart the failed application because the ultrasound system 15 is not operable without the application running. The process manager 200 of the network management station 45 forwards a message to the process manager 100 of the ultrasound system 15 to restart the application, and the ultrasound system 15 is again fully operational.

The log monitor 220 can also tell the alert manager 215 to send a message (e.g., a page) to local service personnel. If the local service personnel is at the remote service center 50, he can cause the process manager 300 at the remote service center 50 to retrieve more detailed error data from the network management station 45. The log monitor 220 can also send a network message with detailed error data to the report application 345 running at the remote service center 50. Alternatively, the remote service center 50 can routinely collect the data stored in the log 260 of the network management station 45 by initiating a file transfer through the respective file transfer processes 225, 325 and process managers 200, 300. It is preferred that the remote service center 50 use a Web browser to contact the network management station 45. The report application 345 can then process the collected data for a specific network device, a set of network devices, or a specific imaging location. As described in more detail below, the process manager 300 of the remote service center 50 can also communicate a command to the process manager 200 of the network management station 45 to command the process manager 200 of the network management station 45 to install software, perform a diagnostic check, or change the configuration of the ultrasound system 15.

As the preceding examples illustrate, the network management station 45 provides several advantages over prior network management models in which a technician at a remote service center is contacted to assess the severity of an error. Because the network management station 45 does intelligent processing of error messages, it does not require a human operator. Further, by analyzing and responding to errors from the ultrasound systems on the network 10, the network management station 45 can reduce the number of times that service personnel is contacted to respond to errors in the ultrasound systems on the network 10. This allows a service provider to operate in a more efficient manner by being able to plan a service call for a future date instead of having to immediately respond to a reported problem. Accordingly, the network management station 45 provides a more efficient and less costly network management model, thereby allowing cost reduction of services while increasing the quality and response to user issues. Further, by automatically contacting service personnel or the remote service center 50 when an important error occurs, the network management station 45 improves the speed of service to the troubled ultrasound system, thereby providing a sophisticated and cost-effective device management tool.

Providing-Software-Application Embodiments

Figure 5:
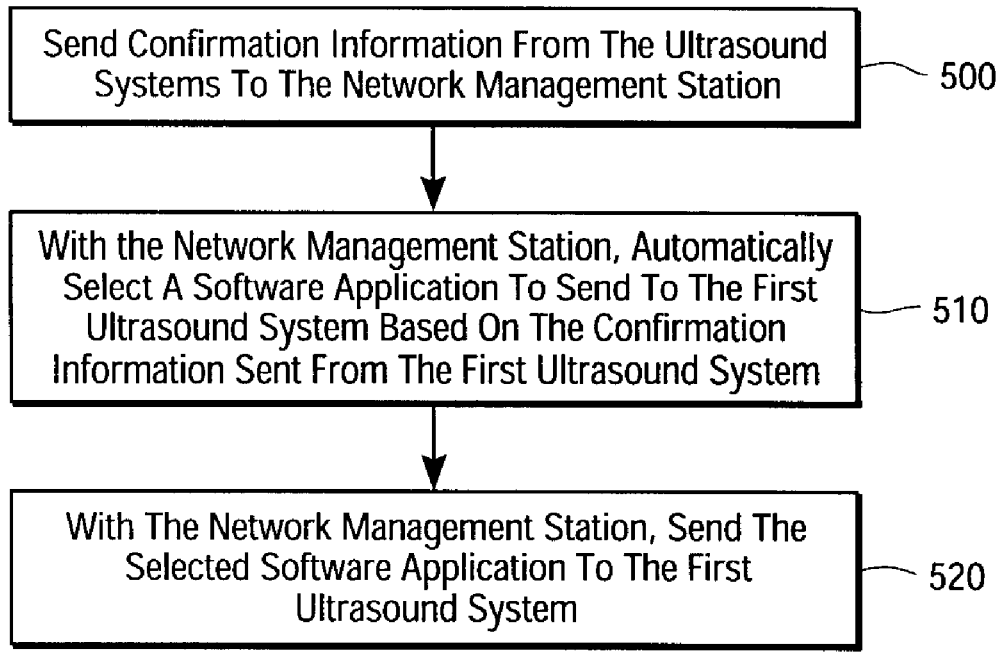
FIG. 5 is a flow chart of a method for providing a software application to a medical diagnostic ultrasound imaging system of a preferred embodiment.

The processor of the network management station 45 can also be used to provide an ultrasound imaging system on the local network 10 with a software application, which can be a new application or an upgrade/update to an application already present on the ultrasound system. This preferred embodiment will be illustrated in conjunction with the flow chart of FIG. 5. In this preferred embodiment, a software application is to be sent from the network management station 45 to the first ultrasound system 15. As shown in the flow chart of FIG. 5, configuration information is sent from the ultrasound systems on the network 10 to the processor of the network management station 45 (act 500). In this way, the network management station 45 will know the configuration of each of the ultrasound systems on the network 10, including the first ultrasound system 15. Next, the processor of the network management station 45 automatically selects a software application to send to the first ultrasound system 15 based on the configuration information sent from the first ultrasound system 15 (act 510). In this way, if the ultrasound system 15 is being used for a specific application (e.g., cardiac imaging), the network management station 45 can select the appropriate software applications to send to the ultrasound system 15 (e.g., cardiac applications instead of GI applications). The software applications from which the processor selects are preferably stored in a storage device on the network management station 45. After the software application has been selected, the processor of the network management station 45 sends the software application to the first ultrasound system 15 (act 520).

There are several actions that can initiate the transmission of a software application from the network management station 45 to the ultrasound system 15. In one embodiment, a software application is sent from the network management station 45 in response to a request from the first ultrasound system 15. For example, the user of the first ultrasound system 15 may need to use a software application that is currently not installed on the first ultrasound system 15. The user can send a request from the first ultrasound system 15 to the network management station 45, or the ultrasound system 15 itself can automatically send the request in response to the user selecting a function on the system 15 that requires an additional software application. In another embodiment, the software application is sent to the first ultrasound system 15 in response to a decision made by the network management station 45. For example, in response to an error message from the ultrasound system 15, the network management station 45 may decide to send a software patch fix to the ultrasound system 15 to remedy the error. As another example, the network management station 45 can send an entire archived software set or operating system to the ultrasound system 15 to allow for a network boot for a clean install. Additionally, the network management station 45 can be programmed to automatically provide the software application at a certain date, for example. In this way, a trial application can be provided to the ultrasound system 15 at a certain time and date as a promotion. In yet another preferred embodiment, the software application is sent to the first ultrasound system 15 in response to a command from the remote service center 50. In this way, software applications (e.g., updates and patches) can be pushed from the remote service center 50. For example, if a user of the ultrasound system 15 requests a new application from the remote service center 50, the remote service center 50 can command the network management station 45 to send the requested application to the ultrasound system 15 rather than directly contact the ultrasound system 15 or send a technician to the site of the ultrasound system 15.

The following is an illustration of this preferred method using the presently preferred implementation set forth in FIG. 4. In this preferred embodiment, the remote service center 50 provides the network management station 45 with the software applications via a remote transmission, while in another preferred embodiment, a local computer 55 provides the software applications to the network management station 45 (e.g., via a CD-ROM on an on-site laptop computer). The software applications are transferred to the software distribution directory 230 on the network management station 45 using the software install process 330 at the remote service center 50 and the process managers 200, 300 and the file transfer processes 225, 325 on the network management station 45 and the remote service center 50. In this example, versions 4.0 and 4.1 of Application 1 are provided to the network management station 45. In operation, the process manager 200 of the network management station 45 analyzes configuration information in the logs provided by the first ultrasound system 15. For example, the logs can inform the process manager 200 that Application 1 on the first ultrasound system 15 is version 4.0. Based on this information, the process manager 200 instructs the file transfer process to select the appropriate software application from the software distribution directory 230 and send it to the first ultrasound system 15. To update Application 1, version 4.1 of Application 1 (instead of version 4.0) would be selected and sent to the first ultrasound system 15. The software install process 130 of the first ultrasound system 15 would then control the software installation. As another example, for a clean installation where the ultrasound system 15 hard disk would need to be repartitioned, the ultrasound system 15 can load its operating system from the network management station's software distribution directory 230 through the local network 10 using the boot manager 140.

In any of the preferred embodiments described above, the network management station 45 can be provided with security features. As described above, it is preferred that the network management station 45 not have a removable disk to prevent the station from being remotely booted and that its operating system refuse to boot in the absence of a root disk with the correct kernel checksum. To provide security to the network, it is preferred that network time protocol be implemented to synchronize log files, that "finger" and "who" commands be disabled, and that NFS mounted files and "r" commands (e.g., rlogin and rsh) be prohibited. As a further security measure, it is preferred that the network management station 45 provide a firewall and IP masquerading within the network to ensure adequate security (i.e., to deny any service unless expressly permitted). Authentication of remote users and commands are preferably performed via asymmetric encryption or secure hash, and remote commands preferably require authentication and application level gateways. Further, any communication to and from the network management station 45 can be encrypted. A suitable encryption technique is described in U.S. patent application Ser. No. 09/052,466 ("Ultrasound Method and System for Enabling an Ultrasound Device Feature"), filed Mar. 31, 1998, which is assigned to the Assignee of the present invention and is hereby incorporated by reference.

There are several alternatives that can be used with these preferred embodiments. As a first matter, it should be noted that parts or all of the embodiments described above can be used alone or in combination. For example, the error-analysis embodiments can be used alone or in conjunction with the providing-software-application embodiments. In one alternate embodiment, instead of the network management station 45 being a stand-alone device, the network management station 45 is part of another device on the network 10, such as the image management server 30 or another ultrasound system. In yet another alternate embodiment, the functionality of the network management station 45 is distributed to two or more components on the network 10. For example, the image management server 30 can implement the process manager, file transfer process, and software distribution directory, while the first review station 35 can implement the log manager and log monitor. Also, while the preferred embodiments described above were discussed in conjunction with an ultrasound imaging system, the preferred embodiments can also be used with other, non-imaging devices on the network, such as a review station and an image management server.

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

APPENDIX I

It is preferred that the error messages be formatted to include the following fields: date, time, system type and serial number, software domain, error number, software detail number, and message text. The following are three examples of the preferred format and output fields:

Mar 08 16:32:01 S50343 im: M1234I 20021 Sys. boot complete
Mar 08 16:34:01 S50343 im: M1236I 10009 Sys. net. connection check successful
Mar 08 16:34:01 S50343 im: M1236F 10009 Sys. boot failure

| | |
|---|---|
| MMM | Three character month name in English |
| DD | The day of the month |
| HH | The hour in 24-hour time |
| MM | The minute |
| SS | The second |
| T | Type of system |
| SN | Serial number |
| ST | Approximate system state when the error occurred (encoded): |
| | "bt" OS boot code generated the message |
| | "bi" Imaging boot scripts generated the message |
| | "pb" post-boot code generated the message |
| | "ni" non-imaging code running after post-boot |
| | "in" installation |
| | "si" service user interface |
| | "dv" development mode |
| | "im" imaging code |

APPENDIX I-continued

Error Message Detail:

D Domain (M MSM; U UISC; D Display; A Acquisition; P low-level plumbing such as the operating system, boot scripts, harmony; T Test; I Image Analysis)
LLLL 4-digit log message number. This is a unique number within the domain name. It is used as an index into a message file to convert the message from a number to text.
S System Action.

I - information
w - warning
e - error
f - fatal
d - dire
I - information + Forward to NMS
W - warning + Forward to NMS
E - error + Forward to NMS
F - fatal + Forward to NMS
D - dire + Forward to NMS
DDDDD 5 digit programmer's detail about the log message number.
TEXT The string found in the log message file for this domain. Separate per-domain files are maintained.

What is claimed is:

1. A medical diagnostic ultrasound imaging system network comprising:
a first medical diagnostic ultrasound imaging system comprising:
a first transducer;
a first transmit beamformer;
a first receive beamformer, the first transmit beamformer and the first receive beamformer being coupled with the first transducer;
a first processor coupled with the first transmit beamformer and the first receive beamformer;
a second medical diagnostic ultrasound imaging system comprising:
a second transducer;
a second transmit beamformer;
a second receive beamformer, the second transmit beamformer and the second receive beamformer being coupled with the second transducer;
a second processor coupled with the second transmit beamformer and the second receive beamformer; and
a network management station comprising a third processor networked with the first and second medical diagnostic ultrasound imaging systems, wherein the network management station is in communication with a remote service center;
wherein the first and second processors are operative to send an error message from the first and second medical diagnostic ultrasound imaging systems, respectively, to the third processor, and wherein the third processor is operative to automatically analyze and respond to the error message without contacting the remote service center.

2. The invention of claim 1, wherein the third processor is locally networked with the first and second medical diagnostic ultrasound imaging systems.

3. The invention of claim 1, wherein the network management station comprises a storage device.

4. For use in a medical diagnostic ultrasound imaging system network comprising first and second medical diagnostic ultrasound imaging systems coupled with a network management station in communication with a remote service center and comprising a processor, a method for responding to an error message from the first medical diagnostic ultrasound imaging system with the processor of the network management station, the method comprising:

(a) sending an error message from the first medical diagnostic ultrasound imaging system to the processor of the network management station;
(b) with the processor of the network management station, automatically analyzing the error message from the first medical diagnostic ultrasound imaging system; and
(c) with the processor of the network management station, automatically responding to the error message sent from the first medical diagnostic ultrasound imaging system based on the analysis performed in (b) without contacting the remote service center.

5. The invention of claim 4, wherein (c) comprises sending a command from the processor to the first medical diagnostic ultrasound imaging system.

6. The invention of claim 5, wherein the error message indicates an application exception, and wherein the command instructs the first medical diagnostic ultrasound imaging system to restart the application.

7. The invention of claim 4, wherein (c) comprises logging the error message.

8. The invention of claim 4, wherein (c) comprises sending a message to service personnel.

9. The invention of claim 4, wherein (c) comprises sending a message to a remotely-located processor from the processor in the medical diagnostic ultrasound imaging system network.

10. The invention of claim 9 further comprising logging the error message with the remotely-located processor.

11. The invention of claim 9 further comprising, with the remotely-located processor, providing the processor in the medical diagnostic ultrasound imaging system network with a response to the error message.

12. The invention of claim 4, wherein (c) comprises sending a software application to the first medical diagnostic ultrasound imaging system.

13. A medical diagnostic ultrasound imaging system network comprising:
a first medical diagnostic ultrasound imaging system comprising:
a first transducer;
a first transmit beamformer;
a first receive beamformer, the first transmit beamformer and the first receive beamformer being coupled with the first transducer;
a first processor coupled with the first transmit beamformer and the first receive beamformer;
a second medical diagnostic ultrasound imaging system comprising:
a second transducer;
a second transmit beamformer;
a second receive beamformer, the second transmit beamformer and the second receive beamformer being coupled with the second transducer;
a second processor coupled with the second transmit beamformer and the second receive beamformer; and
a third processor networked with the first and second medical diagnostic ultrasound imaging systems;
wherein the first and second processors are operative to send an error message from the first and second medical diagnostic ultrasound imaging systems, respectively, to the third processor, and wherein the third processor is operative to automatically analyze and respond to the error message;

wherein the third processor is part of a third medical diagnostic ultrasound imaging system.

14. A medical diagnostic ultrasound imaging system network comprising:

a first medical diagnostic ultrasound imaging system comprising:
a first transducer;
a first transmit beamformer;
a first receive beamformer, the first transmit beamformer and the first receive beamformer being coupled with the first transducer;
a first processor coupled with the first transmit beamformer and the first receive beamformer;

a second medical diagnostic ultrasound imaging system comprising:
a second transducer;
a second transmit beamformer;
a second receive beamformer, the second transmit beamformer and the second receive beamformer being coupled with the second transducer;
a second processor coupled with the second transmit beamformer and the second receive beamformer; and a third processor networked with the first and second medical diagnostic ultrasound aging systems;

wherein the first and second processors are operative to send an error message from the first and second medical diagnostic ultrasound imaging systems, respectively, to the third processor, and wherein the third processor is operative to automatically analyze and respond to the error message;

wherein the third processor is part of an image management server.

15. For use in a medical diagnostic ultrasound imaging system network comprising first and second medical diagnostic ultrasound imaging systems coupled with a processor, a method for responding to an error message from the first medical diagnostic ultrasound imaging system with the processor, the method comprising:

(a) sending an error message from the first medical diagnostic ultrasound imaging system to the processor;

(b) with the processor, automatically analyzing the error message from the first medical diagnostic ultrasound imaging system; and (c) with the processor, automatically responding to the error message sent from the first medical diagnostic ultrasound imaging system based on the analysis performed in (b);

wherein (b) comprises querying a table with the error message.

16. For use in a medical diagnostic ultrasound imaging system network comprising first and second medical diagnostic ultrasound imaging systems coupled with a processor, a method for responding to an error message from the first medical diagnostic ultrasound imaging system with the processor, the method comprising:

(a) sending an error message from the first medical diagnostic ultrasound imaging system to the processor;

(b) with the processor, automatically analyzing the error message from the first medical diagnostic ultrasound imaging system; and (c) with the processor, automatically responding to the error message sent from the first medical diagnostic ultrasound imaging system based on the analysis performed in (b);

wherein (b) comprises querying a binary decision tree with the error message.

* * * * *